(12) United States Patent
Igney et al.

(10) Patent No.: US 9,258,873 B2
(45) Date of Patent: Feb. 9, 2016

(54) SIGNAL AND POWER SUPPLY TRANSMISSION

(75) Inventors: Jens Igney, Erlangen (DE); Reinhard Steiner, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 192 days.

(21) Appl. No.: 14/127,552

(22) PCT Filed: Jun. 25, 2012

(86) PCT No.: PCT/IB2012/053190
§ 371 (c)(1),
(2), (4) Date: Jun. 5, 2014

(87) PCT Pub. No.: WO2013/001434
PCT Pub. Date: Jan. 3, 2013

(65) Prior Publication Data
US 2014/0376696 A1    Dec. 25, 2014

(30) Foreign Application Priority Data

Jun. 30, 2011 (EP) .................................... 11172079

(51) Int. Cl.
| | | |
|---|---|---|
| *H05G 1/56* | (2006.01) | |
| *H03K 17/691* | (2006.01) | |
| *H05G 1/10* | (2006.01) | |
| *A61B 6/00* | (2006.01) | |

(52) U.S. Cl.
CPC ............... *H05G 1/56* (2013.01); *H03K 17/691* (2013.01); *A61B 6/40* (2013.01); *H05G 1/10* (2013.01)

(58) Field of Classification Search
CPC ......... H05G 1/10; H05G 1/56; H03K 17/691; A61B 6/40
USPC .................................................. 378/101, 114
See application file for complete search history.

(56) References Cited

U.S. PATENT DOCUMENTS 4,361,901 A    11/1982    Daniels et al.
4,685,118 A *  8/1987    Furbee .................... H01J 35/06
                                                    378/114

(Continued)

FOREIGN PATENT DOCUMENTS

JP         9131076      5/1997
JP       2001307933   11/2001

(Continued)

*Primary Examiner* — Courtney Thomas (57) ABSTRACT

The present invention relates to signal and power supply transmission for an X-ray source. In order to provided an improved signal and power supply transmission with reduced constructional complexity and enhanced operation possibilities, an integrated signal and power supply transmission arrangement is provided, comprising a supply board (12), a main board (14), an insulating plate (16), at least one transformer arrangement (18), and at least one signal transmission arrangement (20). The insulating plate is provided between the supply and the main board. The transformer arrangement is provided to supply electric energy to the driving circuit of a transistor, which in turn feeds an X-ray source. The transformer arrangement comprises a primary electric conductor arranged on the supply board to cause electromagnetic induction in a secondary electric conductor arranged on the main board. The signal transmission arrangement is adapted to transmit a signal between the supply board and the main board; wherein the signal transmission arrangement comprises at least a first optical signal transmission device provided on the supply board, and a second optical signal transmission device (30) provided on the main board. The insulating plate is light-transmissive at least in the part between the first and second optical signal transmission device. The first and the second optical signal transmission devices are arranged in an optical connection path.

12 Claims, 7 Drawing Sheets

(56) References Cited

U.S. PATENT DOCUMENTS 4,807,105 A 2/1989 Varjasi et al.
2008/0107235 A1 5/2008 Sundaram

FOREIGN PATENT DOCUMENTS

| WO | WO2007138525 | 12/2007 |
|----|--------------|---------|
| WO | WO2009131429 | 10/2009 |

* cited by examiner

SIGNAL AND POWER SUPPLY TRANSMISSION

CROSS-REFERENCE TO PRIOR APPLICATIONS

This application is the U.S. National Phase application under 35 U.S.C. §371 of International Application Serial No. PCT/IB2012/053190, filed on Jun. 25, 2012, which claims the benefit of European Application Serial No. 11172079.3, filed on Jun. 30, 2011. These applications are hereby incorporated by reference herein.

FIELD OF THE INVENTION

The present invention relates to signal and power supply transmission. The invention in particular relates to an integrated signal and power supply transmission arrangement, a high voltage switch, an X-ray generator, and a method for generating a high voltage supply for an X-ray source.

BACKGROUND OF THE INVENTION

The transmission of a signal and the transmission of electrical power, i.e. power supply, is used, for example, in high voltage applications, such as in a gantry of computed tomography systems. High voltage switches are used, for example, to provide the necessary electrical energy to an X-ray tube as well as the respective switching commands for the operation of the X-ray tube. U.S. Pat. No. 4,685,118 describes a circuit for controlling energization of a cathode. A switching transistor is coupled to a photodiode outside the housing via a light pipe. It has been shown, for example, that a continuous cycling between on and off of a switch can mean a restriction with respect to possible switching schemes. A further disadvantage can be seen in the fact that separate signal transmission devices result in complex design structures as well as in increased manufacturing costs.

SUMMARY OF THE INVENTION

Thus, there exists a need for an improved signal and power supply transmission with reduced constructional complexity and enhanced operation possibilities.

This object is solved by the subject-matter of the independent claims, wherein further embodiments are incorporated in the dependent claims.

It should be noted that the following described aspects of the invention apply also for the integrated signal and power supply transmission arrangement, the high voltage switch, the X-ray generator and the method for generating a high voltage supply for an X-ray source.

According to a first aspect of the invention, an integrated signal and power supply transmission arrangement for a high voltage switch is provided, comprising a supply board, a main board, an insulating plate, at least one transformer arrangement, and at least one signal transmission arrangement. The insulating plate is provided between the supply board and the main board. The at least one transformer arrangement is provided to supply electric energy to the driving circuit of a transistor, which in turn feeds an X-ray source, wherein the at least one transformer arrangement comprises a primary electric conductor arranged on the supply board to cause electromagnetic induction in a secondary electric conductor arranged on the main board. The at least one signal transmission arrangement is adapted to transmit a signal between the supply board and the main board, wherein the at least one signal transmission arrangement comprises at least a first optical signal transmission device provided on the supply board, and a second optical signal transmission device provided on the main board. The insulating plate is light-transmissive at least in the part between the first and the second optical signal transmission devices. The first and the second optical signal transmission devices are arranged in an optical connection path.

According to the present invention, the insulating plate is light-transmissive for an optical link. The term "optical link" preferably relates to a link with visible light, but also refers to a link with infrared light, or to a link with electromagnetic waves in the radar range, e.g. radar coupling.

The term "electric conductor" refers to any type of electric conductor capable of causing electromagnetic induction. For example, the electric conductors may be provided as coils or other spiral-formed conductors.

According to an exemplary embodiment of the invention, at least one of the primary and secondary electric conductors is provided with a circumferential structure, and at least one of the first and second signal transmission devices is provided in a concentric manner with the electric conductor.

According to a further exemplary embodiment, the at least one signal transmission arrangement comprises at least one pair of light transmitter and light receiver.

For example, the first optical signal transmission device is provided as a first light-transmitter and the second optical signal transmission device is provided as a first light receiver, wherein the first light transmitter and the first light receiver form a first signal path. As a further example, the first optical signal transmission device also comprises a second light receiver and a second optical signal transmission device also comprises a second light transmitter, wherein the second light receiver and the second light transmitter form a second signal path, wherein the first and the second signal paths have opposite signal directions.

According to a second aspect of the invention, a high voltage switch is provided, comprising a transistor and an integrated signal and power supply transmission arrangement according to one of the above-mentioned aspects and examples. The transistor is provided on the main board. The transformer arrangement is arranged to provide electric power to drive the transistor, and the second optical signal transmission device is connected to the driving circuit of the transistor for signal transmission.

According to an aspect of the invention, the optical transmission is used for the exact synchronization of all transistors; the transformational coupling supplies the (for example, MosFET) transistor gates with sufficient driving energy. Both, i.e. inductive and optical transmission are responsible for the control of the transistors; the actual energy, switched in the drain-source-circuit, is provided by a generator.

According to a further exemplary embodiment, a plurality of transistors is provided, which transistors are series connected. A signal transmission arrangement is provided for each one of the transistors, and the transistors are provided on a common main board.

A transformer arrangement may be provided for each of the transistors.

According to another example, at least one transformer arrangement is provided as a shared transformer arrangement, comprising a primary electric conductor on the supply board to cause electromagnetic induction in at least two secondary electric conductors arranged on the main board, wherein each of the at least two secondary electric conductors supplies a separate transistor input.

According to an exemplary embodiment of the invention, the insulating plate is adapted such that it acts as a light conductor between directly adjacent signal transmission arrangements.

According to a further exemplary embodiment, an optical separation is provided between portions of the insulating plate of adjacent signal transmission arrangements.

Of course, optical separation and light conductor effect can be provided in combination, wherein, for example, a first number of adjacent signal transmission arrangements are provided with a separation, and a second number of adjacent signal transmission arrangements are provided with the light conductor effect.

According to a third aspect of the invention, an X-ray generator is provided, comprising an X-ray source with a cathode and an anode and a high voltage switch according to one of the above-mentioned aspects and examples. The cathode and the anode are provided with electric energy from the high voltage switch in order to emit an electron beam from the cathode to the anode for the generation of X-ray radiation.

According to a fourth aspect of the present invention, a method for generating a high voltage supply for an X-ray source is provided, comprising the following steps: a) providing primary electrical energy to a primary electric conductor of a transformer arrangement, thereby causing electromagnetic induction in a secondary electric conductor resulting in secondary electrical energy, wherein the primary electric conductor and the secondary electric conductor are separated by an insulating plate; b) providing the secondary electrical energy to a transistor; c) providing a primary control signal to a first optical signal transmission device to generate an optical signal; d) transmitting the optical signal through the insulating plate to a second optical signal transmission device to generate a secondary control signal, wherein the insulating plate is light-transmissive at least in the part between the first and second optical signal transmission device; and e) providing the secondary control signal to the transistor to switch the transistor.

According to an aspect of the present invention, power supply transmission is combined with signal transmission by providing an insulating plate for a power supply transmission with an electric separation, which insulating plate is transmissive for the signal to be transmitted, which signal is provided as a light signal. Thus, an integrated signal and power supply transmission is provided, which has a minimized number of components and which also consumes only a minimized construction space. The integrated signal and power supply transmission arrangement is thus suitable in particular for computer tomography appliances.

These and other aspects of the invention will become apparent from and elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
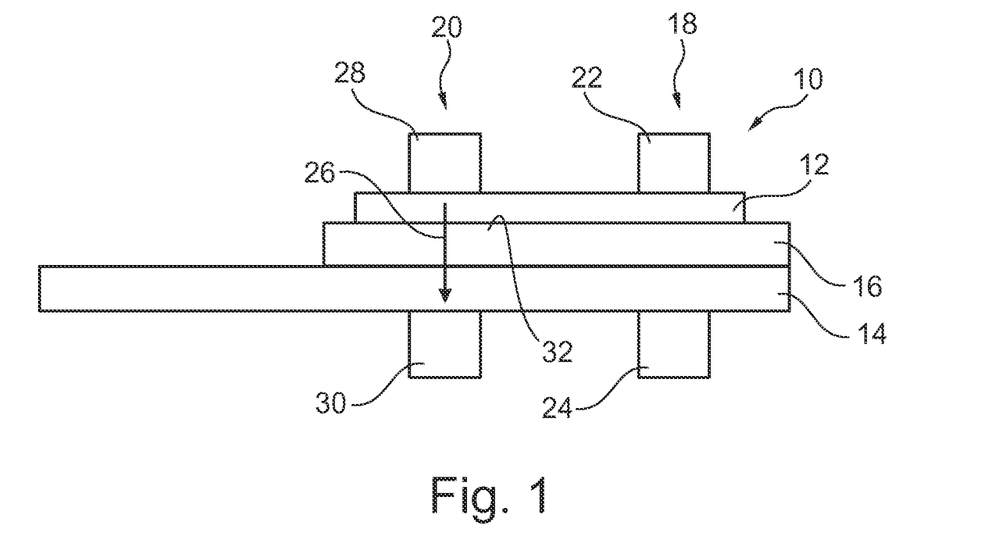
FIG. 1 illustrates an integrated signal and power supply transmission arrangement according to an exemplary embodiment of the invention.

FIG. 1 shows an integrated signal and power supply transmission arrangement 10 for a high voltage switch, comprising a supply board 12, a main board 14, and an insulating plate 16. Further, at least one transformer arrangement 18 and at least one signal transmission arrangement 20 are provided. The insulating plate 16 is provided between the supply board 12 and the main board 14.

The at least one transformer arrangement 18 is provided to supply electric energy to an X-ray source, wherein the at least one transformer arrangement 18 comprises a primary electric conductor 22 arranged on the supply board 12 to cause electromagnetic induction (not further shown) in a secondary electric conductor 24 arranged on the main board 14.

The at least one signal transmission arrangement 20 is adapted to transmit a signal, indicated by an arrow 26, between the supply board 12 and the main board 14. It is noted that the signal indicated with the arrow 26 is shown with a particular direction in FIG. 1 as an example only; thus, the signal can also be transmitted in the reverse direction. The at least one signal transmission arrangement 20 comprises at least a first optical signal transmission device 28 provided on the supply board 12, and a second optical signal transmission device 30 provided on the main board 14.

The insulating plate 16 is light-transmissive at least in the part between the first and second optical signal transmission devices 28, 30. The insulating plate is also referred to as isolating plate. Further, the first and the second optical signal transmission devices 28, 30 are arranged in an optical connection.

The term "high voltage" refers to a voltage of at least 1 kV.

As indicated in FIG. 1, the insulating plate 16 is arranged as a continuous plate provided with a light-transmissive portion 32 between the first and the second optical signal transmission devices 28, 30.

According to a further example (not shown), the insulating plate is provided with a hole arranged between the first and the second optical signal transmission devices 28, 30, in order to provide an optical connection between the optical signal transmission devices.

According to a further example, the high voltage switch, for which the integrated signal and power supply transmission arrangement 10 is provided, is an X-ray high voltage switch.

As mentioned above, the term "optical connection" as well as the terms "optical signal transmission device" and "light-transmissive" refer to electromagnetic radiation provided as visible light, but also includes infrared light and also electromagnetic waves in the radar range, although the latter are usually not referred to as "light".

As also indicated above, the optical signal transmission device 20 is adapted to transmit the signal from the supply board to the main board and/or vice versa to transmit a signal from the main board to the supply board.

For example, the insulating plate is provided as a transparent plate. The insulating plate may be made from Polymethylmethacrylat (PMMA). It is noted that the insulating plate only needs to be transparent in the area where the signal 26 is transmitted. Thus, the rest of the insulating plate may be coloured or provided otherwise to be opaque or at least with a reduced light transmission characteristic in those parts. However, with respect to assembly and costs, the provision of a transparent insulating plate is preferable. Of course, it is also possible to provide the insulating plate made from different materials such that in the portion or area of the at least one signal transmission arrangement 20 the respective light-transmissive characteristic is provided and whereas other areas are different therefrom.

Figure 2:
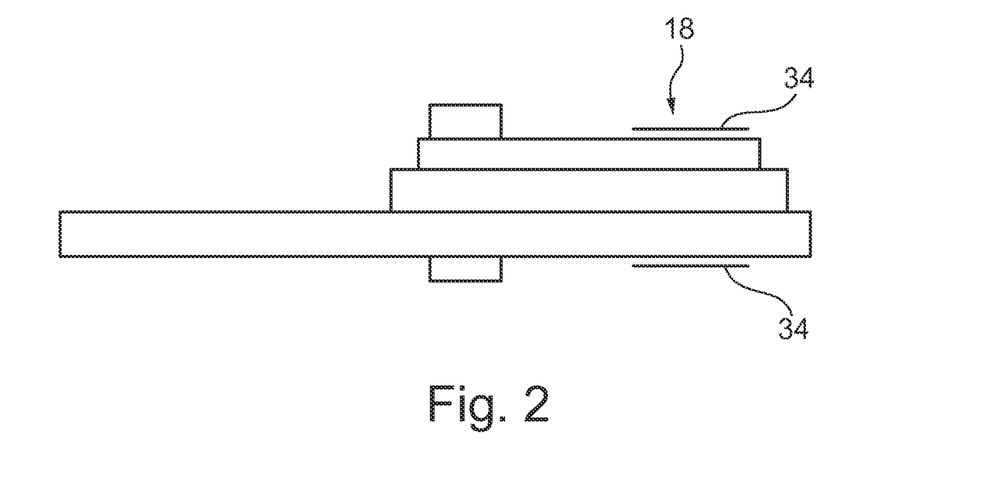
FIGS. 2 to 8 illustrate further examples of integrated signal and power supply transmission arrangements according to the present invention.

As shown in FIG. 2, the electric conductors are provided as coils 34, indicated with a single line only in FIG. 2. For example, the coils may be provided as spiral tracks on the respective board.

For example, the transformer arrangement 18 is provided with a two-part core comprising a primary and a secondary part, between which a gap is provided (not further shown).

According to another example, as indicated in the Figs., the transformer arrangement 18 is provided as a coreless transformer.

Due to the absence of a magnetic core, and also caused by a possible large thickness of the insulating plate, the coils may be regarded as forming a transformer with a not so effective link per se. Nevertheless, by operating the transformer in a resonant manner, and with high frequency, for example, sufficient efficiencies above 70% are provided. Thus, it is possible to avoid smaller coupling factors.

Figure 3:
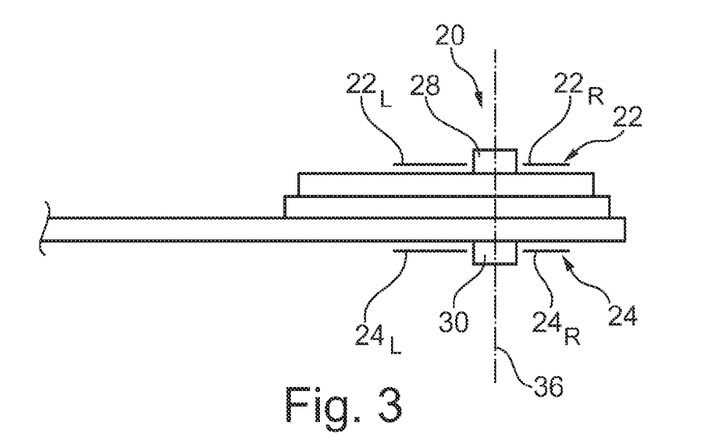

According to a further exemplary embodiment, shown in FIG. 3, at least one of the primary and secondary electric conductors is provided with a circumferential structure, wherein at least one of the first and second signal transmission devices is provided in a concentric manner with the electric conductor. In FIG. 3, both the primary and the secondary electric conductors 22, 24 are provided as coils. The schematic cross-section of FIG. 3 is approximately aligned with the centre of these coils such that the drawing shows the respective left halves of the coils and the respective right halves of the coils, each indicated with the letter "L" and the letter "R", respectively. Of course, instead of the coils, other circumferential structures can be provided, wherein the term "circumferential" refers to a structure of the electric conductor leaving a central area unused in order to be able to provide the first and second signal transmission devices 28, 30 in this centre.

As schematically shown in FIG. 3, the first and second signal transmission devices 28, 30 are thus arranged inside the primary and secondary electric conductors 22, 24. A dotted centre line 36 indicates the concentric arrangement. It is noted that the concentric manner, or concentric arrangement, does not have to be precisely aligned with respect to a geometric centre point or centre line. Of course, a slightly shifted arrangement, wherein one part or component is arranged inside the other part or component, is also possible.

According to a further example, not shown, the first and second signal transmission devices 28, 30 are also provided with a circumferential structure such that it is possible to arrange the primary and secondary electric conductors 22, 24 inside the respective signal transmission device 28, 30.

For example, the term "circumferential structure" refers to a circular or annular structure.

According to a further example, not further shown, it is also possible to provide only one of the first and second signal transmission devices in a concentric manner, for example in case one of the primary and secondary electric conductors 22, 24 is not provided in a circumferential structure (also see below, FIG. 12).

Figure 4:
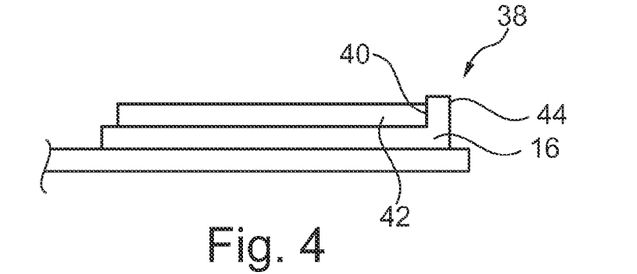

As shown in FIG. 4, according to a further exemplary embodiment, the insulating plate 16 has at least one protruding edge 38 arranged such that at least a part of a front end 40 of an edge 42 of one of the supply board and main board is covered by the insulating plate 16.

The protruding edge increases the dielectric strength. According to a further aspect, as shown in FIG. 4, the protruding edge is provided as an L-shaped edge 44.

Figure 5:
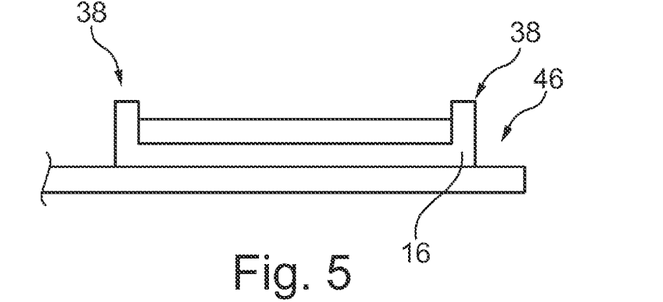

As shown in FIG. 5, the insulating plate 16 is provided with a protruding edge 38 on opposite edges forming a U-shaped cross-section 46.

For example (not further shown), the insulating plate 16 is provided with a protruding circumferential edge. This applies for the above-mentioned examples, as well as the following examples.

Figure 6:
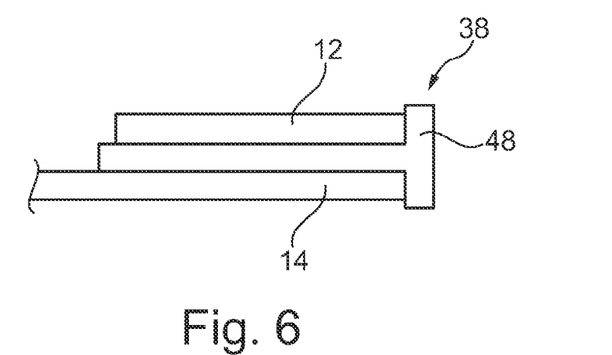

As shown in FIG. 6, the protruding edge 38 is provided as a T-shaped edge 48, covering at least a part of a front end of an edge of the supply board 12 and at least a part of a front end of an edge of the main board 14.

It must be noted that FIGS. 4 to 6 illustrate only the discussed aspects. In other words, the other features shown in FIG. 1, 2, or 3, are not further shown in FIGS. 4 to 6, but of course, do also apply to these figures.

Figure 7:
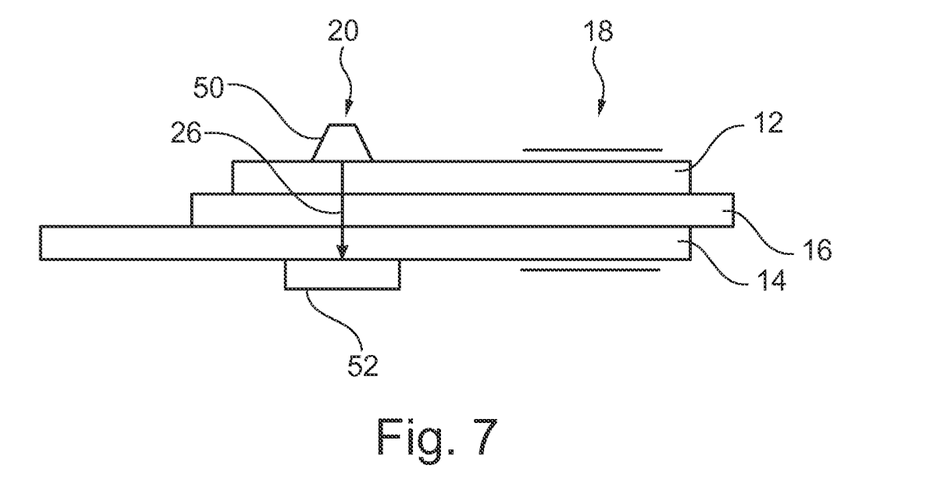

As schematically shown in FIG. 7, the at least one signal transmission arrangement 20 comprises at least one pair of a light transmitter 50 and a light receiver 52. It is noted that the arrangement of the light transmitter 50 and the light receiver 52 can also be provided in the reverse manner, i.e. the light transmitter 50 can be provided on the supply board 12 or on the main board 14, which also applies for the light receiver 52.

It is further noted that the at least one transformer arrangement 18 is only schematically indicated with two lines.

For example, the signal 26 is an optical signal transmitted through the insulating plate 16.

The supply board 12 may comprise at least one light-transmissive opening (not further shown) arranged for transmitting the optical signal, wherein the optical signal transmission device is arranged on the supply board facing away from the insulating plate, as shown in FIG. 7.

The main board may comprise at least one light-transmissive opening arranged for transmitting the optical signal, wherein the optical signal transmission device is arranged on the main board facing away from the insulating plate (as also shown in FIG. 7).

According to a further example (not further shown), the first optical signal transmission device is provided as a first light transmitter and the second optical signal transmission device is provided as a first light receiver. Thus, the first light transmitter and the first light receiver form a first signal path.

According to a further example, the first optical signal transmission device also comprises a second light reference and the second optical signal transmission device also comprises a second light transmitter. Thus, the second light receiver and the second light transmitter form a second signal path, wherein the first and the second signal paths may have opposite signal directions.

Thus, for example, a cascade connection scheme is possible.

Figure 8:
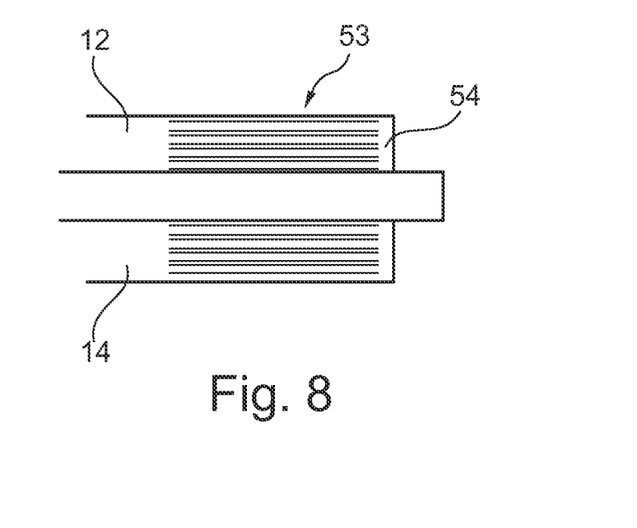

As indicated in FIG. 8, the coils can be provided as spiral tracks 53 in a multilayer stack 54 on the respective board, i.e. on the supply board 12 and/or the main board 14.

Figure 9:
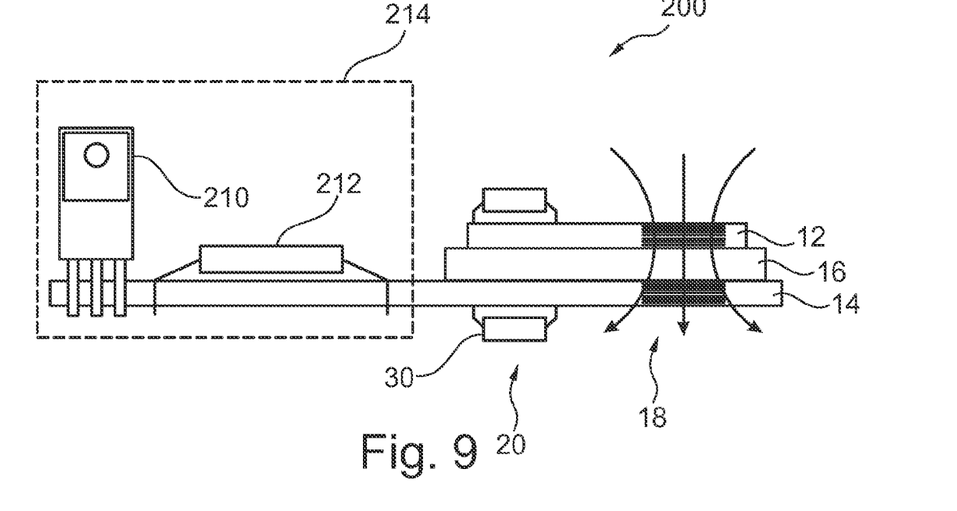
FIG. 9 schematically illustrates a high voltage switch according to an exemplary embodiment of the invention.

According to a further aspect of the present invention, as shown in FIG. 9, a high voltage switch 200 is provided, comprising a transistor 210 and an integrated signal and power supply transmission arrangement 10 according to one of the above described examples and/or embodiments. The transistor 210 is provided on the main board 14. The transformer arrangement 18 is arranged to provide electric power to the transistor. The second optical signal transmission device 30 is connected to the transistor for signal transmission.

It is noted that the connections, for example for the electric power supply, or the signal transmission connection, are not further shown.

For example, a driver 212 for the at least one transistor may be provided, wherein the second optical signal transmission device 30 is connected to the transistor via the driver for signal transmission to the transistor. It is noted that the driver, although shown in FIG. 9, can also be omitted.

According to a further example, the signal transmission is provided to and from a gate terminal of the transistor 210.

According to a further example (not shown), further devices may be arranged on the main board 14, which is also indicated with a dotted frame 214.

Figure 10:
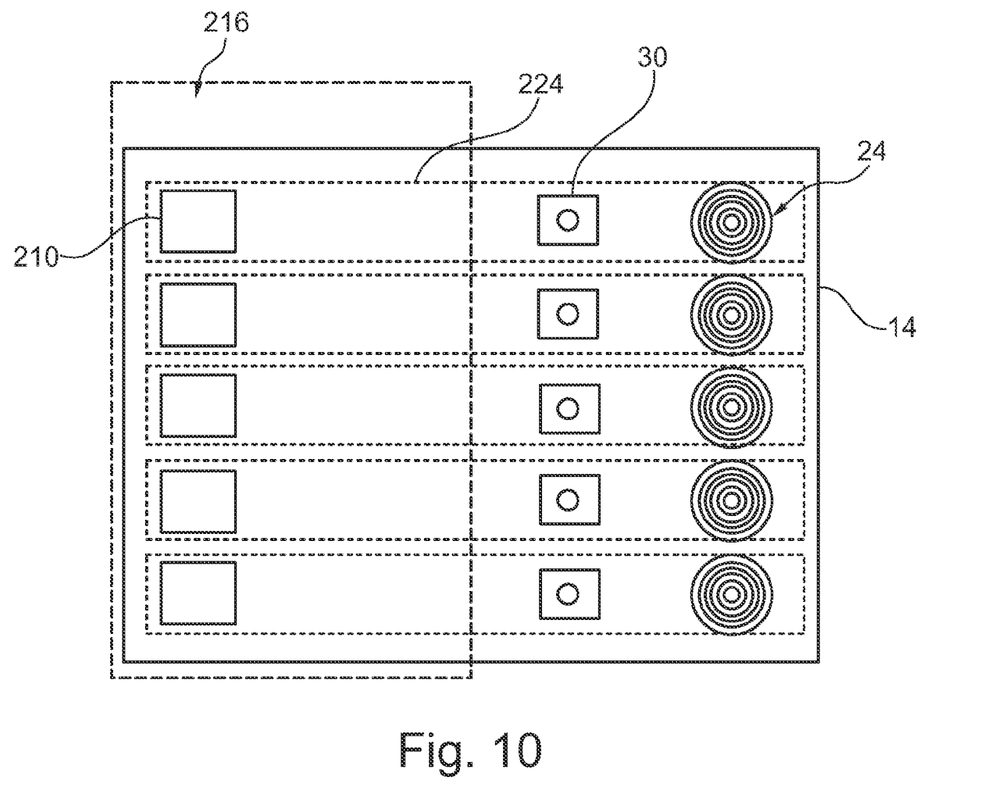
FIGS. 10 to 12 illustrate further examples of high voltage switches according to the present invention.

FIG. 10 illustrates a further example, according to which a plurality 216 of transistors 210 is provided, which transistors are series connected. It is noted that FIG. 10 shows the arrangement in a so-to-speak view from above, whereas FIGS. 1 to 9 are shown as schematic cross-sections from the side.

According to FIG. 10, a signal transmission arrangement 20 is provided for each of the transistors 210. The transistors are provided on a common main board 14.

Figure 11:
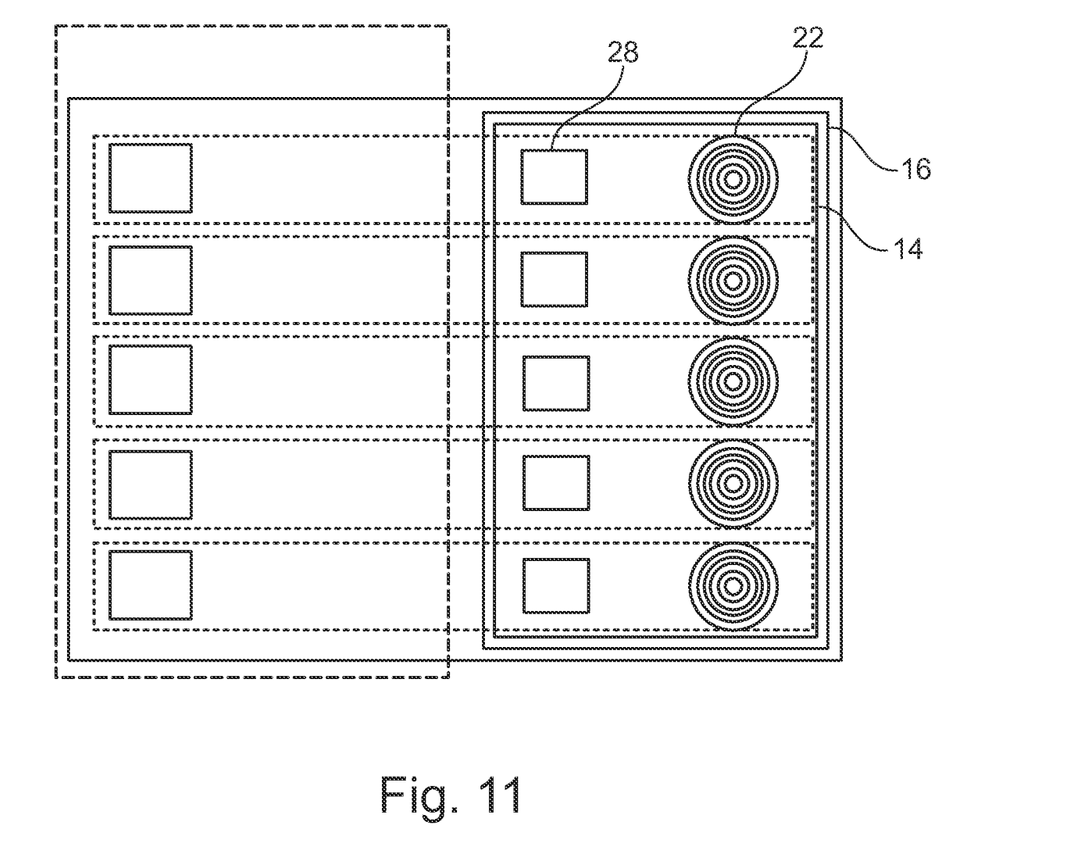

With respect to FIG. 10, it is further noted that FIG. 10 schematically only shows the arrangements concerning the main board 14, whereas in FIG. 11, also the supply board 14 and the insulating plate 16 are shown.

In FIG. 10, also the secondary electric conductors 24 are shown with a coil structure, which also applies to FIG. 11, where the primary electric conductors 22 are also shown with a coil structure. Further, in FIG. 11, the first optical signal transmission devices 28 are indicated, whereas FIG. 10 shows the second optical signal transmission devices 30.

Figure 12:
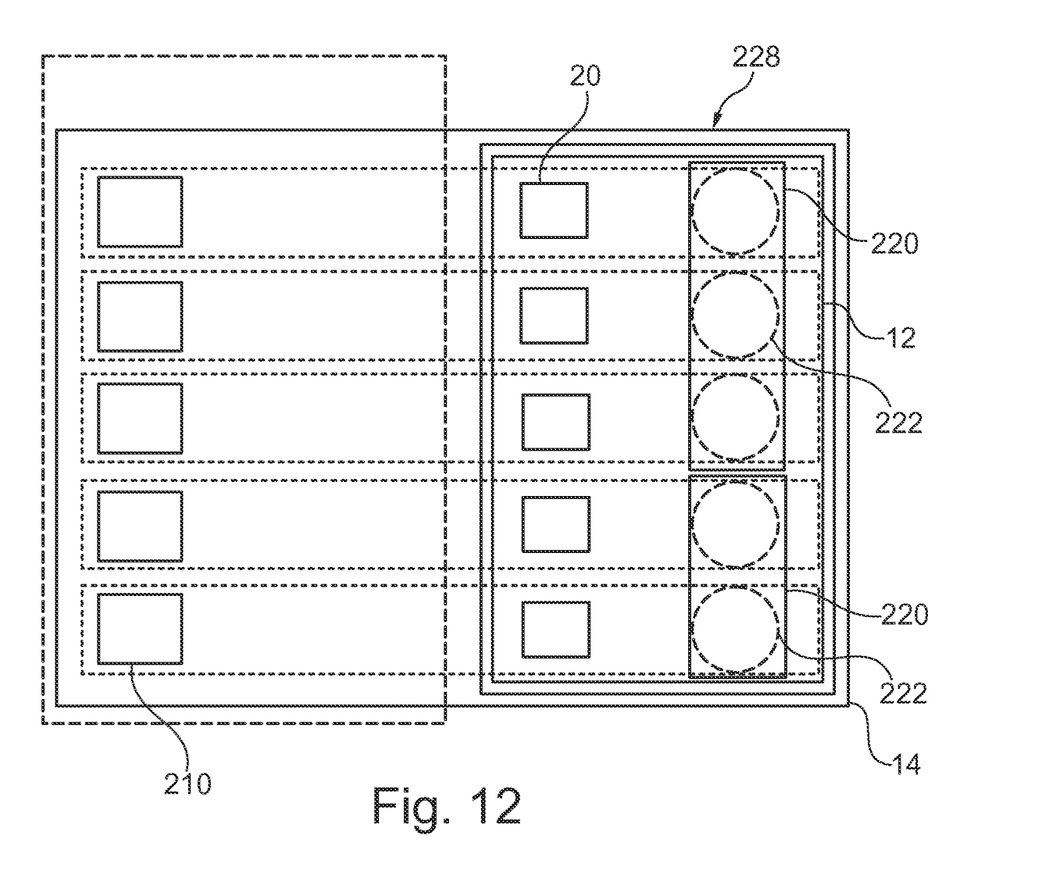

FIG. 12 schematically illustrates a further exemplary embodiment, according to which at least two transformer arrangements 18 are provided as a shared transformer arrangement 218, comprising one primary electric common conductor 220 on the supply board 12 to cause electromagnetic induction in at least two secondary electric conductors 222 arranged on the main board 14, which secondary electric conductors 222 are shown with a dotted circle to indicate their arrangement on the underside of the main board 14 with respect to the illustration of FIG. 12. Each of the at least two secondary electric conductors 222 supplies a separate transistor 210.

FIG. 12 shows an example for a shared transformer arrangement 220 supplying electric energy to three secondary electric conductors 222 in the upper part and a shared transformer arrangement 220 supplying only two secondary electric conductors 222 in the lower half. Further, a signal transmission arrangement 20 is provided for each transistor 210.

According to a further example, as indicated above, a common insulating plate is provided.

For example, also a common supply board may be provided, as indicated in FIG. 12. The primary electric conductors 22 and the first optical signal transmission devices 28 are arranged on the common supply board.

According to an alternative example, a number of supply boards, and/or a number of insulating plates may be provided (not further shown).

According to a further example, which is also shown in relation with FIGS. 10 to 12, but which can also be omitted with respect to the features described in relation with FIGS. 10 to 12, each transistor with the respective transformer arrangement and signal transmission arrangement forms a channel, which is indicated in FIG. 10 with a dotted frame 224. Each channel is operationable on its high voltage potential.

According to a further example (not further shown), the insulating plate is adapted such that it acts as a light conductor between directly adjacent signal transmission arrangements.

For example, in case of parallel controlled switches, a malfunctioning of a signal transmission arrangement can be replaced by the signal of an adjacent signal transmission arrangement.

According to an alternative example (not further shown), an optical separation is provided between portions of the insulating plate of adjacent signal transmission arrangements.

For example, in case of separately controlled switches, optical cross-talk of the optical signal paths can be minimized therewith.

Figure 13:
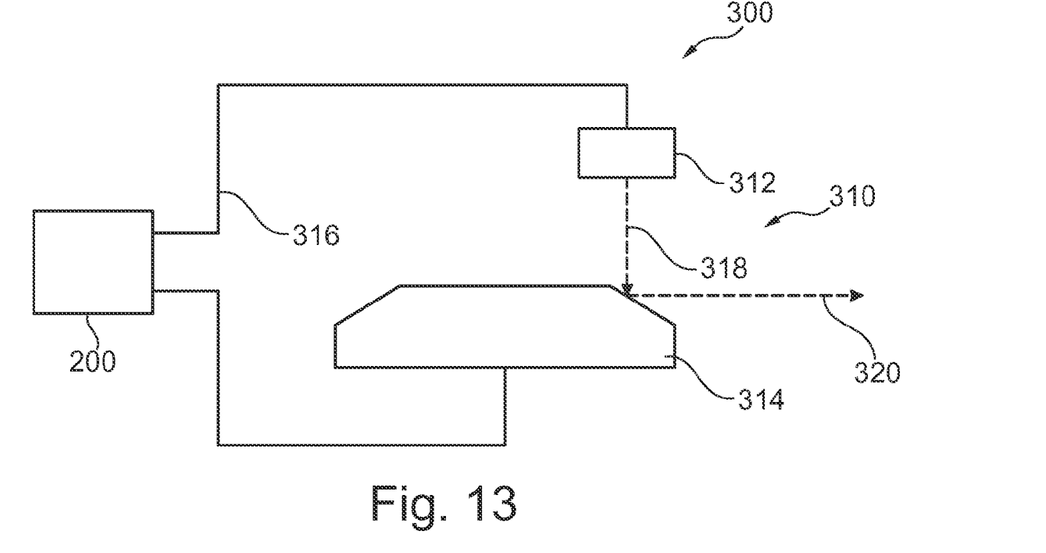
FIG. 13 schematically illustrates an exemplary embodiment of an X-ray generator according to the present invention.

FIG. 13 shows an exemplary embodiment of an X-ray generator 300 comprising an X-ray source 310 with a cathode 312 and an anode 314. Further, a high voltage switch 200 according to one of the above-mentioned described embodiments and examples is provided. The cathode and the anode are provided with electric energy from the high voltage switch, which is schematically indicated with two supply lines 316. The provision of electric energy to the cathode and the anode is provided in order to emit an electron beam 318 from the cathode to the anode for the generation of X-ray radiation 320. It is noted that the X-ray radiation 220 is illustrated with a dotted arrow only, and of course also comprises a cone beam for fan-shaped X-ray beam. It is further noted that the X-ray generator 300 is shown in a very schematic way to illustrate the principles. Of course, necessary parts, such as a vacuum housing, for example, or controlling devices are not further shown.

Figure 14:
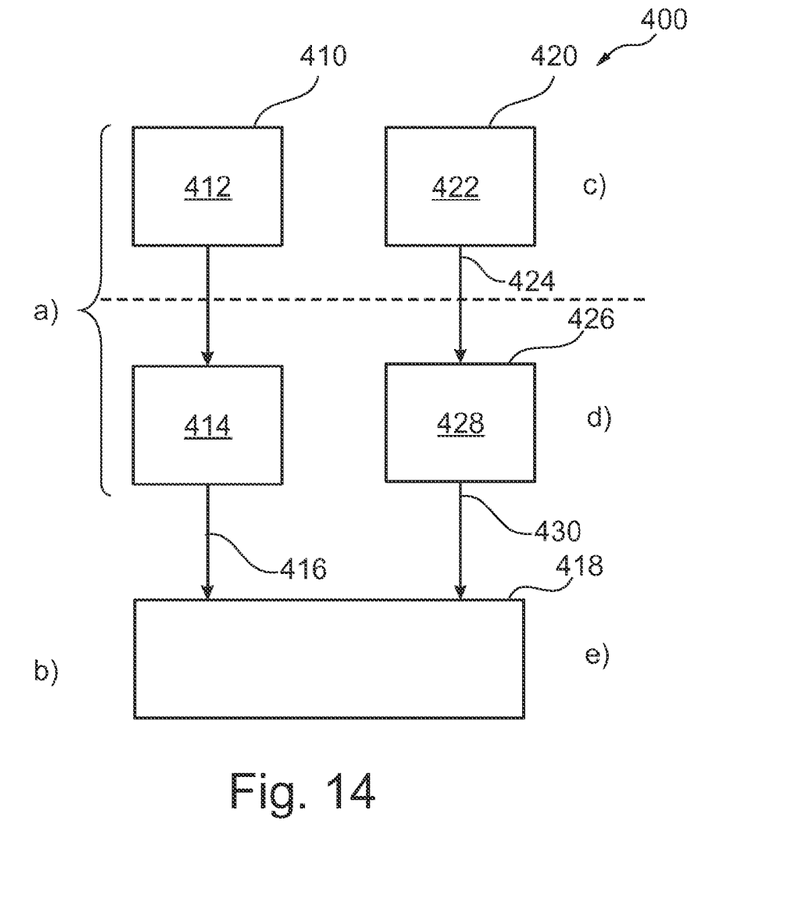
FIG. 14 schematically illustrates basic method steps of a method for generating a high voltage supply for an X-ray source according to an exemplary embodiment of the invention.

FIG. 14 shows a method 400 for generating high voltage supply for an X-ray source according to an exemplary embodiment of the present invention. The method 400 comprises the following steps:

In a first provision step 410, primary electrical energy 412 is provided to a primary electric conductor of a transformer arrangement, thereby causing electromagnetic induction in a secondary electric conductor resulting in secondary electrical energy 214. The primary electric conductor and the secondary electric conductor are separated by an insulating plate.

In a second provision step 416, the secondary electrical energy is provided to a transistor, indicated with a frame 418.

In a third provision step 420, a primary control signal 422 is provided to a first optical signal transmission device to generate an optical signal.

In a transmission step 424, the optical signal is transmitted through the insulating plate to a second optical signal transmission device to generate 426 a secondary control signal 428, wherein the insulating plate is light-transmissive at least in the part between the first and second optical signal transmission device.

Further, in a fourth provision step 430, the secondary control signal 428 is provided to the transistor 418 for a switching of the transistor.

Thus, it is possible to supply the transistor 418 with electric energy as well as with a control signal.

It is noted that the first provision step 410 is also referred to as step a), the second provision step 416 as step b), the third provision step 420 as step c), the transmission step 424 as step d), and the fourth provision step 430 as step e).

In the following, some further aspects are described in relation with the present invention. An integrated signal and power supply transmission according to the invention is suitable for high voltage switches in X-ray systems, for example. For generating high voltages that are used for X-ray generation, high voltage switches may be constructed by series connection of transistors. Each transistor has to be driven by a signal between its gate- and source-terminal. This means that each driver has its reference potential at the source voltage of its transistor. Thus, power has to be provided to the drivers and a signal has to be transmitted for the control of the transistor.

According to the invention, the use of the insulating plate avoids high voltage insulation with complicated geometries, which would be expensive and space consuming. Also, the assembly of several parts of insulating material in an intertwining way is avoided, by the, for example, single piece of plate-shaped insulating material of the invention. As explained above, the power is transferred, for example, by a coreless coil system above and below the plate and the signal is transmitted by light through the transparent insulation and received on the other side.

As shown in FIG. 9, the main board 14 is equipped with transistors 210, and drivers or other devices 212, which have to be supplied with energy and signal. The main board 14 is insulated from the supply board 12 by a plate of transparent electric isolating material 16. By this, all voltage potentials of the main board 14 are well separated from the signal and power source, which are not further shown. The dielectric strength is given by the thickness of the isolating plate 16.

The power supply may be realized by a coreless transformer with coils on each side of the isolating plate 16. The thickness of the plate and, for example, the absence of a magnetic core through the coils may be considered to form a not so effectively linked transformer. However, by operating it resonant and with high frequency, sufficient efficiencies above 70% may be achieved.

Signals from and to the main board 14 can be provided by pairs of light transmitters and receivers. The example of FIG. 9 may be provided with one signal channel with a transmitter above and a receiver below the isolating plate 16. The light shines through a hole in the supply board 12, through the transparent isolating plate 16 and through a hole in the main board 14 to the receiver.

A high voltage switch may then consist of series connected transistors (see also FIG. 10). Each transistor, its driver and supporting circuitry form a so called "channel". Each channel operates on its own high voltage potential. Each channel may be equipped with a backward-sensitive photo diode and a coil realized by spiral tracks in the multilayer stack of the printed circuit board (PCB). An isolating plate, for example made of PMMA (for which the "Plexiglas" is also known), is provided above the supply board. The coil of the supply board may be realized as PCB-coil in the same way as its counterpart. One or both coils may be realized by wire to increase coupling. Coil sizes may also be different; for example, one transmitter coil supplies two or more receive coils.

Further, additional PCBs may be stacked above the supply PCB to make use of the available space.

A high voltage switch with an integrated signal and power supply transmission according to the invention can be realized very compact and space optimized. This is a technology-enabling feature for switching high voltages in dense assemblies like a gantry of a computed tomography system.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An integrated signal and power supply transmission arrangement (10) for a high voltage switch, comprising:
   a supply board (12);
   a main board (14);
   an insulating plate (16);
   at least one transformer arrangement (18); and
   at least one signal transmission arrangement (20);
   wherein the insulating plate is provided between the supply board and the main board;
   wherein the at least one transformer arrangement is provided to supply electric energy to the driving circuit of a transistor, which in turn feeds an X-ray source; and
   wherein the at least one transformer arrangement comprises a primary electric conductor (22) arranged on the supply board to cause electromagnetic induction in a secondary electric conductor (24) arranged on the main board;
   wherein the at least one signal transmission arrangement is adapted to transmit a signal (26) between the supply board and the main board; and wherein the at least one signal transmission arrangement comprises at least a first optical signal transmission device (28) provided on the supply board, and a second optical signal transmission device (30) provided on the main board;
   wherein the insulating plate is light-transmissive at least in the part between the first and second optical signal transmission device; and
   wherein the first and the second optical signal transmission devices are arranged in an optical connection path.

2. Arrangement according to claim 1, wherein at least one of the primary and secondary electric conductors is provided with a circumferential structure; and
   wherein at least one of the first and second signal transmission devices is provided in a concentric manner (36) with the electric conductor.

3. Arrangement according to claim 1, wherein the insulating plate has at least one protruding edge (38) arranged such that at least a part of a front end of an edge of one of the supply board and main board is covered by the insulating plate.

4. Arrangement according to claim 1, wherein the at least one signal transmission arrangement comprises at least one pair of light transmitters (50) and light receivers (52).

5. Arrangement according to claim 1, wherein the primary electric conductor and the secondary electric conductor are arranged as coils being provided as spiral tracks (53) in a multilayer stack (54) on the respective board.

6. A high voltage switch (200), comprising:
a transistor (210); and
an integrated signal and power supply transmission arrangement (10) according to claim 1;
wherein the transistor is provided on the main board;
wherein the transformer arrangement is arranged to provide electric power to drive the transistor; and
wherein the second optical signal transmission device is connected to the driving circuit of the transistor for signal transmission.

7. High voltage switch according to claim 6, wherein a plurality (216) of transistors is provided, which transistors are series connected;
wherein a signal transmission arrangement is provided for each one of the transistors; and
wherein the transistors are provided on a common main board.

8. High voltage switch according to claim 6, wherein each transistor with the respective transformer arrangement and signal transmission arrangement forms a channel (224); and
wherein each channel is operationable on its own high voltage potential.

9. High voltage switch according to claim 6, wherein the insulating plate is adapted such that it acts as a light conductor between directly adjacent signal transmission arrangements.

10. High voltage switch according to claim 6, wherein an optical separation is provided between portions of the insulating plate of adjacent signal transmission arrangements.

11. X-ray generator (300), comprising:
an X-ray source (310) with a cathode (312) and an anode (314); and
a high voltage switch (200) according to claim 6;
wherein the cathode and the anode are provided with electrical energy from the high voltage switch in order to emit an electron beam from the cathode to the anode for the generation of X-ray radiation.

12. A method (400) for generating a high voltage supply for an X-ray source, comprising the following steps:
a) providing (410) primary electrical energy (412) to a primary electric conductor of a transformer arrangement thereby causing electromagnetic induction in a secondary electric conductor resulting in secondary electrical energy, wherein the primary electric conductor and the secondary electric conductor are separated by an insulating plate;
b) providing (416) the secondary electrical energy to a transistor;
c) providing (420) a primary control signal (422) to a first optical signal transmission device to generate an optical signal;
d) transmitting (424) the optical signal through the insulating plate to a second optical signal transmission device to generate (426) a secondary control signal (428), wherein the insulating plate is light-transmissive at least in the part between the first and second optical signal transmission device; and
e) providing (430) the secondary control signal to the transistor to switch the transistor.

* * * * *